(12) United States Patent
Bresler et al.

(10) Patent No.: US 7,838,713 B2
(45) Date of Patent: Nov. 23, 2010

(54) PROCESS FOR SEPARATING PARA-XYLENE FROM A MIXTURE OF C8 AND C9 AROMATIC HYDROCARBONS

(75) Inventors: Leonid Bresler, Northbrook, IL (US); Stanley J. Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 337 days.

(21) Appl. No.: 12/146,901

(22) Filed: Jun. 26, 2008

(65) Prior Publication Data

US 2009/0326306 A1 Dec. 31, 2009

(51) Int. Cl.
*C07C 7/12* (2006.01)

(52) U.S. Cl. .................... 585/828; 585/820; 585/825; 585/822

(58) Field of Classification Search .................... None
See application file for complete search history.

(56) References Cited

U.S. PATENT DOCUMENTS

| | | | | |
|---|---|---|---|---|
| 3,392,113 | A | 7/1968 | Rosset | 208/310 |
| 3,510,423 | A | 5/1970 | Neuzil et al. | 208/310 |
| 3,686,342 | A | 8/1972 | Neuzil | 260/674 SA |
| 3,696,107 | A | 10/1972 | Neuzil | 260/674 SA |
| 3,813,452 | A | 5/1974 | Bieser | 260/674 SA |
| 4,101,594 | A | 7/1978 | Howard, Jr. | 260/668 A |
| 4,594,144 | A | 6/1986 | James, Jr. et al. | |
| 4,864,069 | A * | 9/1989 | Zinnen | 585/828 |
| 4,886,930 | A | 12/1989 | Zinnen | 585/828 |
| 5,012,038 | A | 4/1991 | Zinnen | 585/828 |
| 5,057,643 | A | 10/1991 | Zinnen | 585/828 |
| 5,171,922 | A | 12/1992 | Anderson | 585/805 |
| 5,177,295 | A | 1/1993 | Oroskar et al. | 585/805 |
| 5,849,981 | A * | 12/1998 | Kulprathipanja | 585/828 |
| 6,573,418 | B2 | 6/2003 | Miller et al. | 585/826 |
| 6,600,083 | B2 | 7/2003 | Doyle et al. | 585/828 |
| 6,627,783 | B2 | 9/2003 | Doyle et al. | 585/828 |
| 6,689,929 | B2 | 2/2004 | Williams et al. | 585/825 |
| 6,878,855 | B2 | 4/2005 | Deckman et al. | 585/477 |
| 2007/0299289 | A1 | 12/2007 | Bresler et al. | 585/323 |

OTHER PUBLICATIONS

U.S. Appl. No. 12/146,975, filed Dec. 31, 2009, Bresler et al.
US Office Action dated Jul. 16, 2010 for U.S. Appl. No. 12/146,975.
Reply dated Sep. 28, 2010 to US Office Action dated Jul. 16, 2010 for U.S. Appl. No. 12/146,975.

* cited by examiner

*Primary Examiner*—Tam M Nguyen
(74) *Attorney, Agent, or Firm*—David J Piasecki

(57) ABSTRACT

The process includes at least two adsorptive separation zones to separate para-xylene from a feed stream comprising C8 aromatic hydrocarbons and at least one C9 aromatic hydrocarbon component. An adsorbent comprising X or Y zeolite and a heavy desorbent are used in the first adsorptive separation zone to produce an extract stream comprising para-xylene and a raffinate stream comprising para-xylene depleted C8 aromatic hydrocarbons, the C9 aromatic hydrocarbon, and the desorbent. The raffinate stream is separated in a raffinate distillation zone to produce a stream comprising the first desorbent component and the C9 aromatic hydrocarbon which stream is further separated in a second adsorptive distillation zone to produce a stream comprising the desorbent and a C9 aromatic hydrocarbon stream.

20 Claims, 4 Drawing Sheets

US 7,838,713 B2

PROCESS FOR SEPARATING PARA-XYLENE FROM A MIXTURE OF C8 AND C9 AROMATIC HYDROCARBONS

FIELD OF THE INVENTION

The present invention pertains to a process for the separation of para-xylene from a mixture of C8 aromatic hydrocarbons containing at least one C9 aromatic hydrocarbon. In particular, the process includes at least two adsorptive separation steps.

BACKGROUND OF THE INVENTION

Para-xylene is an important raw material in the chemical and fiber industries. For example, terephthalic acid derived from para-xylene is used to produce polyester fabrics. Para-xylene is usually separated from a mixture of para-xylene and at least one other C8 aromatic hydrocarbon by either crystallization, adsorptive separation, or a combination of these two techniques.

U.S. Pat. No. 3,392,113 discloses a cyclic process for the separation of a feed mixture of fluid compounds by contacting the feed with a solid sorbent, such as molecular sieves, selective for at least one compound of said feed mixture, and thereafter passing a fluid desorbent into contact with the sorbent to displace the resulting selectively sorbed compound, said desorbent ordinarily containing trace quantities of aromatic and/or oxygenate impurities which undesirably alter the kinetics, or rates of sorption and desorption of the aforesaid process, over a number of sorption-desorption cycles, the method of stabilizing the kinetics by contacting the desorbent with a separate bed of solid sorbent, prior to utilizing the desorbent in the desorption step, to remove said impurities.

U.S. Pat. No. 5,012,038 recognizes the common use of para-diethylbenzene (p-DEB) as a desorbent for the separation of para-xylene from C8 aromatic hydrocarbon mixtures. It is also known that use of p-DEB as the desorbent limits the C9 aromatics in the feed mixture to less than about 0.1 wt %. This requirement is usually met by first distilling the feed in a so-called xylene splitter column. Otherwise, the C9 aromatic hydrocarbons would gradually build up in the desorbent as it is recycled in the process because C9 aromatics are difficult to separate from p-DEB by simple fractionation and the desorbent must be recycled for economic reasons.

U.S. Pat. No. 5,012,038 and other patents such as U.S. Pat. No. 4,886,930; U.S. Pat. No. 5,057,643; U.S. Pat. No. 5,171,922; U.S. Pat. No. 5,177,295; and U.S. Pat. No. 5,495,061 disclose the use of desorbents having higher boiling points than p-DEB to separate para-xylene from a feed mixture having a C9 aromatic hydrocarbon content greater than 0.1 wt %. The C9 aromatics are then separated from the higher boiling desorbent by fractionation. However, despite the benefits provided by the higher boiling adsorbents, p-DEB continues to be a frequently used desorbent for the adsorptive separation of para-xylene.

SUMMARY OF THE INVENTION

The invention relates to processes for separating para-xylene from a feed stream comprising C8 aromatic hydrocarbons and at least one C9 aromatic hydrocarbon component. In an embodiment, the process may comprise contacting an adsorbent with the feed stream and a first desorbent stream comprising a first desorbent component in a first adsorptive separation zone to produce an extract stream comprising para-xylene and a raffinate stream comprising the para-xylene depleted C8 aromatics, the C9 aromatic hydrocarbon component and the first desorbent component; separating the raffinate stream in a raffinate distillation zone to produce a second desorbent stream comprising the first desorbent component and the C9 aromatic hydrocarbon component; separating the second desorbent stream in a second adsorptive distillation zone to produce a C9 aromatic hydrocarbon stream and a third desorbent stream comprising the first desorbent component.

In another embodiment, the invention may comprise separating para-xylene from a feed stream comprising C8 aromatic hydrocarbons and at least one C9 aromatic hydrocarbon component the process comprising:

(a) contacting a first adsorbent comprising a Y zeolite or an X zeolite with the feed stream and a first desorbent stream comprising a first desorbent component having a boiling point of at least about 150° C. in a first adsorptive separation zone to produce a first extract stream comprising para-xylene and the first desorbent component and a first raffinate stream comprising para-xylene depleted C8 aromatic hydrocarbons, the C9 aromatic hydrocarbon component, and the first desorbent component;

(b) passing the first extract stream to an extract distillation zone to produce a second desorbent stream comprising the first desorbent component and a para-xylene product stream;

(c) passing the first raffinate stream to a raffinate distillation zone to produce a third desorbent stream comprising the first desorbent component and the C9 aromatic hydrocarbon component and a raffinate product stream comprising the para-xylene depleted C8 aromatic hydrocarbons; and (d) passing at least a portion of the third desorbent stream and a desorbent stream comprising a second desorbent component to a second adsorptive separation zone comprising a second adsorbent to produce a second extract stream comprising the first desorbent component and the second desorbent component and a second raffinate stream comprising the C9 aromatic hydrocarbon component and the second desorbent component.

In an embodiment, the first desorbent component is para-diethylbenzene (p-DEB). In another embodiment, the first adsorptive separation zone operates in a simulated moving bed mode. In a further embodiment, the first desorbent stream may comprise up to 25 wt % of C9 aromatic hydrocarbons. Other embodiments of the present invention encompass further details the descriptions of which, including preferred and optional features are hereinafter disclosed.

Thus, in one aspect the invention provides greater flexibility by enabling the adsorptive separation of a C9 aromatic hydrocarbon component from a desorbent component used in the adsorptive separation of para-xylene from feed mixtures comprising C8 aromatic hydrocarbons and at least one C9 aromatic hydrocarbon. In another aspect, the invention provides greater flexibility by enabling the adsorptive separation of para-xylene from the feed mixture wherein the desorbent stream may comprise up to 25 wt % C9 aromatic hydrocarbons.

The Figures are intended to be illustrative of the present invention and are not intended to limit the scope of the invention as set forth in the claims. The drawings are simplified schematic diagrams showing exemplary embodiments of process flow schemes, including process zones, helpful for an understanding of the invention. Details of the process zones, well known in the art, such as pumps, control valves, instrumentation, heat-recovery circuits, and similar hardware which are non-essential to an understanding of the invention are not illustrated.

DETAILED DESCRIPTION OF THE INVENTION

Two adsorptive separation steps or zones are used to separate para-xylene from a feed stream comprising C8 aromatic hydrocarbons and at least one C9 aromatic hydrocarbon component. As used herein, the term "zone" can refer to one or more equipment items and/or one or more sub-zones. Equipment items may include, for example, one or more vessels, heaters, separators, exchangers, conduits, pumps, compressors, and controllers. Additionally, an equipment item can further include one or more zones or sub-zones.

The feed stream is a mixture comprising at least two C8 aromatic hydrocarbons; para-xylene, and at least one of meta-xylene, ortho-xylene, and ethylbenzene. The feed stream also comprises at least one C9 aromatic hydrocarbon component, such as any of the isomers of propylbenzene, methylethylbenzene, and trimethylbenzene. The feed stream may comprise several or all of the C8 and C9 aromatic hydrocarbons, for example, when the feed is derived from one or more oil refining processes such as catalytic reforming, stream cracking, crystallizer mother liquors, transalkylation, and xylene isomerization.

The feed to be processed by this invention may contain as much as 25 wt % C9 aromatics hydrocarbons. Feed streams having at least about 0.1 wt % C9 aromatics are contemplated for use in this process. In an embodiment, the feed stream may comprise from about 0.3 wt % to about 5 wt % C9 aromatic hydrocarbons. In another embodiment, the feed stream may comprise from about 6 wt % to about 15 wt % C9 aromatics. In an embodiment, the feed stream may not contain more than about 10 ppm-mass C10+ aromatic hydrocarbons.

Figure 1:
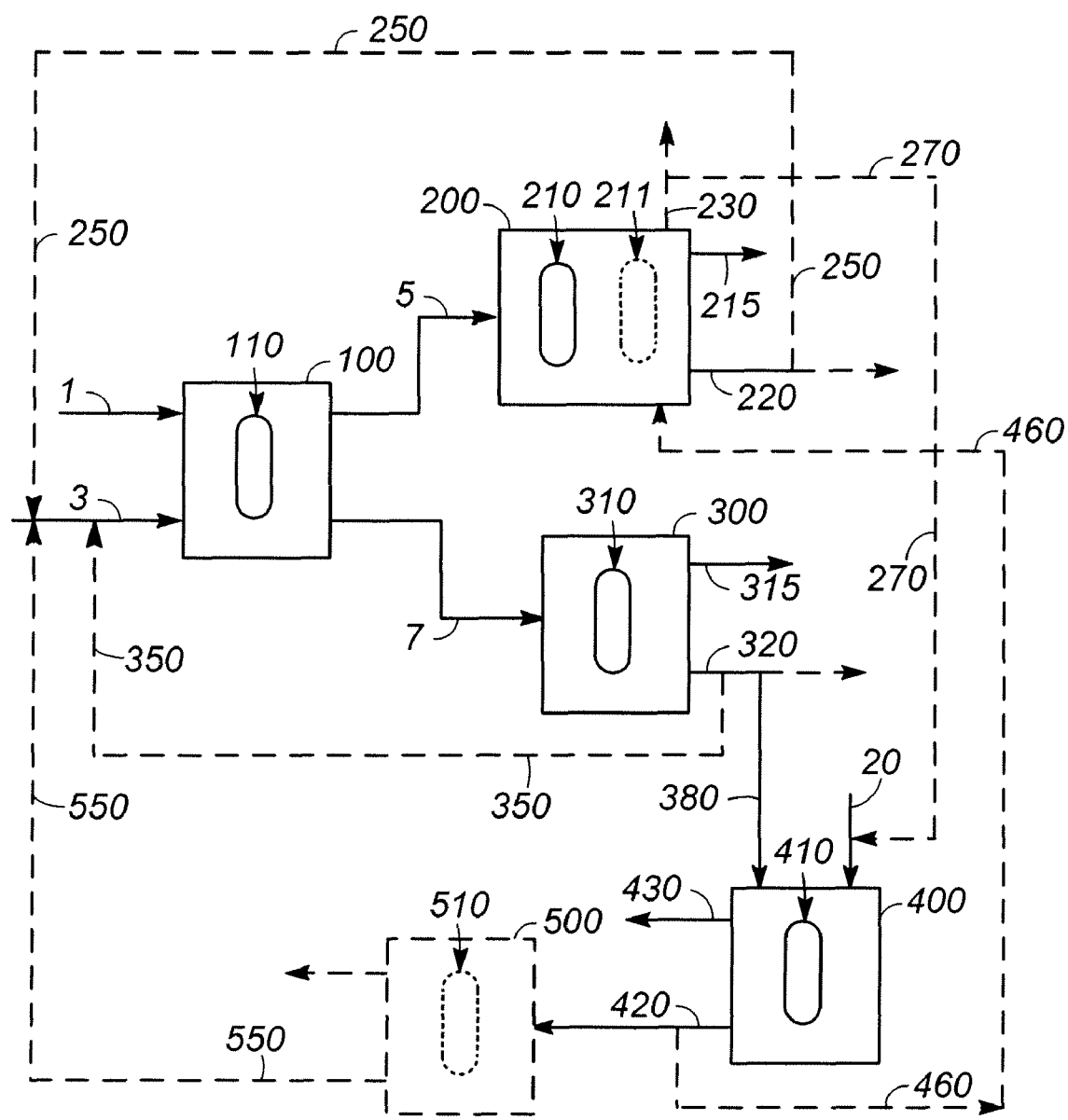
FIG. 1 is a simplified flow scheme of an embodiment of the invention.

FIG. 1 illustrates the flow scheme of an embodiment of the present invention. The feed stream and a desorbent stream are introduced to adsorptive separation zone 100 via feed conduit 1 and desorbent conduit 3, respectively. Adsorptive separation zone 100 comprises adsorbent chamber 110 containing an adsorbent selective for para-xylene over the other C8 aromatic hydrocarbons in the feed. Adsorptive separation zone 100 produces an extract stream carried by extract conduit 5 and a raffinate stream carried by raffinate conduit 7. As shown in the Figures, reference numbers of the streams and the lines or conduits in which they flow are the same. For example, reference number 7 may be used with equal accuracy as raffinate conduit 7, raffinate line 7, raffinate stream 7, and raffinate stream carried by raffinate conduit 7.

Adsorptive separation processes are well known in the art. In brief summary, a feed stream and desorbent stream are introduced to an adsorbent chamber which may include one or more vessels containing an adsorbent. During an adsorption step, the adsorbent contacts the feed and selectively retains a feed component or a class of feed components relative to the remaining feed components. The selectively retained feed component(s) are released or desorbed from the adsorbent by contacting the adsorbent with the desorbent. Thus, the adsorptive separation process produces an extract stream comprising the selectively adsorbed component or class of components and a raffinate stream comprising the remaining feed components that are less selectively adsorbed. The desorbent stream may comprise one or more desorbent components and use of multiple desorbent streams is also known in the art. The extract and raffinate streams passing from the adsorbent chamber typically also comprise one or more desorbent components.

A variety of adsorptive separation techniques are well known in the art including fixed bed such as operating in a batch or swing bed mode, moving bed, and simulated moving bed (SMB). The invention is not intended to be limited by the particular adsorptive separation technique or mode of operation. Additional information regarding adsorptive separation principles and detail are readily available, e.g., Kirk-Othmer Encyclopedia of Chemical Technology Vol. 1, 3rd ed., Adsorptive Separation (Liquids) pp 563-581, 1978 and Preparative and Production Scale Chromatography edited by G. Ganetsos and P. E. Barker, 1993.

As these various adsorptive separation processes operate on the same basic chromatographic separation principles, the following discussion of adsorbents and desorbents applies to the various adsorptive separation techniques or modes. The functions and properties of adsorbent and desorbents in the chromatographic separation of liquid components are well-known, but for reference thereto, U.S. Pat. No. 4,642,397 is herein incorporated by reference.

Adsorbents which are selective for para-xylene relative to the other C8 aromatic isomers are suitable for use in adsorptive separation zone 100. X and Y zeolites are well known in the art for separating para-xylene from other C8 aromatic hydrocarbons. Optionally, these zeolites may containing FUPAC Group 1 or 2 metal ions at exchangeable cation sites. In an embodiment, the adsorbent comprises X zeolite or Y zeolite. Optionally, the adsorbent may comprise barium, potassium, or both barium and potassium.

It is also known that crystalline aluminosilicates, i.e., zeolites, are used in adsorptive separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers, or silica are generally used.

Desorbent stream in line or conduit 3 used in adsorptive separation zone 100 may comprise one or more desorbent components. Suitable desorbent components are "heavy", i.e., they have a boiling point of at least about 150° C. In an embodiment, a desorbent component has a boiling point greater than about 160° C. In another embodiment, a desorbent component has a boiling point greater than about 170° C. Examples of desorbent components in stream 3 suitable for use in adsorptive separation zone 100 include: para-diethylbenzene, diethyltoluene, tetralin, alkyl and dialkyl tetralin derivatives, indane, naphthalene, methylnaphthalene, para-dimethylnaphthalene, and mixtures thereof. In an embodiment, desorbent stream 3 comprises para-diethylbenzene (p-DEB).

In an embodiment the instant invention recognizes that desorbent introduced to adsorptive separation zone 100 may comprise as much as 25 wt % C9 aromatics hydrocarbons. In an embodiment, desorbent stream 3 may comprise at least about 0.7 wt % C9 aromatics. In another embodiment, the C9 aromatic hydrocarbon content of the desorbent stream in line 3 introduced to adsorptive separation zone 100 ranges from about 1 wt % to about 5 wt %; in another embodiment, the range is from about 3 wt % to about 15 wt % C9 aromatics.

In adsorptive separation zone 100, adsorption conditions will include a temperature range from about 20° C. to about 300° C. In an embodiment the adsorption temperature will range from about 20° C. to about 250° C.; in another embodiment the range is from about 40° C. to about 200° C. The adsorption pressure is sufficient to maintain liquid phase, which may be from about 1 barg to about 40 barg. Desorption conditions may include the same range of temperatures and pressure as used for adsorption conditions. In a fixed bed embodiment, adsorptive separation zone 100 may use vapor phase desorption conditions to minimize the amount of desorbent that remains on the adsorbent when feed is next introduced.

Raffinate stream in conduit 7 removed from adsorptive separation zone 100 comprises a desorbent component and the less strongly adsorbed feed components such as ethylbenzene, ortho-xylene, meta-xylene, and most of the C9 aromatics. Although there may be a small amount of para-xylene present, the raffinate stream C8 aromatics may be referred to as para-xylene depleted C8 aromatics. Extract stream in conduit 5 removed from adsorptive separation zone 100 comprises a desorbent component and the most strongly adsorbed feed components including para-xylene and, if present, toluene and para-methylethylbenzene.

As illustrated in FIG. 1, extract stream 5 withdrawn from adsorptive separation zone 100 is passed to extract distillation zone 200. Extract distillation zone 200 comprises extract distillation column 210 and produces para-xylene product stream in line 215 and a desorbent stream removed in conduit 220. Extract product stream 215 may comprise substantially all of the para-xylene in extract stream 5 from adsorptive separation zone 100. As used herein, the term "substantially all" can mean an amount generally of at least 90%, preferably at least 95%, and optimally at least 99%, by weight, of a compound or class of compounds in a stream. In an embodiment, para-xylene product stream 215 is the overhead or light stream from extract distillation column 210 and desorbent stream 220 is the bottoms or heavy stream from distillation column 210. In an embodiment, at least a portion of desorbent stream 220 removed from extract distillation zone 200 may be recycled via optional conduit 250 to provide at least a portion of desorbent stream 3 used in adsorptive separation zone 100. Thus, a recycle conduit providing fluid communication from extract distillation zone 200 to adsorptive separation zone 100 may be the portions of lines 220, 250, and 3 defining the fluid flow path between the zones. That is, here as in the remainder of the description, conduits providing fluid communication may comprise multiple conduits or portions thereof to define a desired fluid flow path.

Those of ordinary skill in the art will understand that the process flow and connections of various zones described herein is sufficient to practice the invention. Unless otherwise stated, the exact connection point within the zones is not essential to the invention. For example, it is well known in the art that a stream to a distillation zone may be sent directly to the column, or the stream may first be sent to other equipment within the zone such as heat exchangers, to adjust temperature, and/or pumps to adjust the pressure. Likewise, streams leaving a zone may pass directly from a distillation column or they may first pass through an overhead or reboiler section before leaving the distillation zone.

Extract distillation zone 200 may also produce additional product streams. As illustrated in FIG. 1, a product stream lighter than para-xylene may be removed from extract distillation zone by optional conduit 230. For example, this embodiment may be used when light impurities in extract stream 5 such as toluene are removed to enable the para-xylene product 215 to meet desired purity specifications. Extract distillation zone 200 may be configured and operated as well known in the art to make three or more product streams, e.g. adding a side draw to extract column 210, using a dividing wall distillation column, and/or including multiple distillation columns such as optional extract finishing distillation column 211 illustrated in FIG. 1.

Para-methylethylbenzene (p-MEB) may also be present in extract stream 5 from adsorptive separation zone 100 and may be distributed in various ratios between the para-xylene 215 and desorbent 220 products of extract distillation zone 200. Factors that impact the p-MEB distribution between the products include parameters such as the design and operation of the distillation column and the boiling point(s) of the desorbent component(s) employed. As recognized herein, desorbent stream 3 introduced to adsorptive separation zone 100 may contain up to about 25 wt % C9 aromatic hydrocarbons, which may include p-MEB. As it is desirable for economic reasons to recycle desorbent in the process, unacceptable accumulation of p-MEB in extract distillation zone desorbent stream 220 may be managed in a number of ways.

In an embodiment, the content of p-MEB in feed stream 1 to adsorptive separation zone 100 may be limited such that the amount of p-MEB in feed stream 1 is not more than about 0.05 wt % of the para-xylene in feed stream 1. In an option not illustrated, a purge stream may remove a portion of desorbent containing p-MEB from line 220 and desorbent of higher purity may be introduced as make-up to the flow scheme. In another embodiment, design and operation of extract distillation column 210 increases the amount of p-MEB in para-xylene product 215. Although it is often desired for para-xylene product 215 to contain at least 99.7 wt % para-xylene, it is not always necessary to remove p-MEB from para-xylene product 215. For example, where para-xylene product is oxidized to make terephthalic acid, oxidation of p-MEB results in the same product. Therefore, not removing p-MEB from para-xylene product 215 may actually be beneficial.

As illustrated in FIG. 1, raffinate stream 7 from adsorptive separation zone 100 is passed to raffinate distillation zone 300. Raffinate distillation zone 300 comprises raffinate distillation column 310 and produces raffinate product stream 315 and desorbent stream 320. In an embodiment, the overhead or light stream from raffinate distillation column 310 is raffinate product stream 315 and the bottoms or heavy stream from distillation column 310 is desorbent stream 320. Raffinate product stream 315 may comprise substantially all of the C8 aromatic hydrocarbons (the para-xylene depleted C8 aromatic hydrocarbons) in raffinate stream 7 from adsorptive separation zone 100. Desorbent stream 320 removed from raffinate distillation zone 300 may comprise substantially all the desorbent in raffinate stream 7 removed from adsorptive separation zone 100. In an embodiment, at least a portion of desorbent stream 320 produced by raffinate distillation zone 300 may be recycled via optional conduit 350 to provide at least a portion of desorbent stream 3 introduced used in adsorptive separation zone 100.

C9 aromatic hydrocarbons have boiling points that range from about 152° C. to about 176° C. Therefore, some of the C9 aromatic hydrocarbons in raffinate stream 7 from adsorptive separation zone 100 will pass to raffinate distillation zone desorbent stream 320 if the boiling point of the desorbent component is not sufficiently high such as when p-DEB is the desorbent component. Adsorptive separation zone 400 prevents unacceptable accumulation of C9 aromatic hydrocarbons in desorbent stream 3 which may be recycled to adsorptive separation zone 100. Adsorptive separation zone 400 may also be used in embodiments where the desorbent component has a higher boiling point than p-DEB. Although it may be possible to separate higher boiling desorbents from C9 aromatics via distillation, the instant invention provides an alternate route to manage the C9 aromatic content for such desorbents that does not require the raffinate distillation column to provide desorbent free of C9 aromatics.

The feed stream 380 to adsorptive separation zone 400 comprises at least a portion of desorbent stream 320 from raffinate distillation zone 300, which comprises a desorbent component from the first adsorptive separation zone 100 and C9 aromatic hydrocarbons. Thus, conduits 320 and 380 or portions thereof which provide fluid communication from raffinate distillation zone 300 to second adsorptive separation zone 400 may also be described as a C9 aromatic hydrocarbon conduit. As discussed for adsorptive separation zone 100, the invention is not intended to be limited by the particular adsorptive separation technique or mode of operation and any of the techniques or modes previously mentioned may be employed in adsorptive separation zone 400. Adsorptive separation zone 400 also requires a desorbent stream which is provided by conduit 20. To avoid confusion, the term "first desorbent component" will refer to desorbent used in the first adsorptive separation zone 100 while the term "second desorbent component" will refer to desorbent introduced by conduit 20 and used as desorbent in the second adsorptive separation zone 400.

In an embodiment, adsorptive separation zone 400 adsorption conditions may include a temperature range from about 20° C. to about 300° C.; in another embodiment the temperature range is from about 20° C. to about 250° C.; optionally from about 40° C. to about 200° C. The adsorption pressures are sufficient to maintain liquid phase, which may be from about 1 barg to about 40 barg. Desorption conditions may include the same range of temperatures and pressures as used for adsorption conditions. In a fixed bed embodiment, second adsorptive separation zone 400 may use vapor phase desorption conditions to minimize the amount of second desorbent component remaining on the adsorbent when stream 380 is introduced to begin the next adsorption/desorption cycle.

Adsorptive separation zone 400 comprises adsorbent chamber 410 containing a second adsorbent and produces an extract stream carried by conduit 420 and a raffinate stream carried by conduit 430. In an embodiment, the second adsorbent is selective for para aromatic isomers over other aromatic isomers including the C9 aromatic component. For example, the second adsorbent may comprise an X or a Y zeolite. Optionally, these zeolites may contain IUPAC Group 1 or 2 metal ions at exchangeable cation sites. The second adsorbent may optionally comprise barium, potassium, or both barium and potassium. Because the first desorbent component is suitable for a para selective first adsorbent, it may be selectively retained by the para selective second adsorbent over the C9 aromatic hydrocarbon component. The second desorbent component may be heavy, for example, selected from the group of possible first desorbent components such as, para-diethylbenzene, diethyltoluene, tetralin, alkyl and dialkyl tetralin derivatives, indane, naphthalene, methylnaphthalene, and para-dimethylnaphthalene; other than the first desorbent component itself.

In another embodiment, the second adsorbent has selectivity for the first desorbent components which have molecular diameters comparable to or smaller than para-diethylbenzene (p-DEB) over the C9 aromatic hydrocarbon component. For example, the second adsorbent may comprise an MFI type zeolite as classified by Structure Commission of the International Zeolite Association (available at web site www.iza-structure.org/databases). Thus, first desorbent components suitable for this embodiment include p-DEB, tetralin, indane, naphthalene, methylnaphthalene, para-dimethylnaphthalene. As before, the second desorbent component may be selected from this same group other than the first desorbent component itself. The second adsorbent may be the same as the first adsorbent, or the second adsorbent may be different from the first adsorbent. For either the para selective or molecular diameter selective adsorbents, the first desorbent component will be discharged from second adsorptive separation zone 400 in extract stream 420 while the C9 aromatic component will be discharged in raffinate stream 430.

The second desorbent used in adsorptive separation zone 400 may comprise one or more components. For example, light desorbent components such as benzene and toluene are suitable second desorbents and may contain small amounts of non-aromatics, e.g. less than about 10 wt %. In an embodiment, the second desorbent component has a boiling point that differs from the boiling points of the first desorbent component and C9 aromatic component by at least 5° C. Use of second desorbents heavier than the first desorbent may provide energy savings if they are separated as discussed below in optional steps and zones. In an embodiment, the first desorbent component is p-DEB and the second desorbent component is benzene, toluene, tetralin, naphthalene, methylnaphthalene, or para-dimethylnaphthalene.

Raffinate stream in conduit 430 removed from adsorptive separation zone 400 comprises the second desorbent component and C9 aromatic component. In an embodiment not illustrated, raffinate stream 430 is fractionated in a distillation zone to produce a C9 aromatic product stream and a stream comprising the second desorbent component which may be recycled to second adsorptive separation zone 400.

Extract stream in conduit 420 removed from adsorptive separation zone 400 comprises the first desorbent component and the second desorbent component. As illustrated in FIG. 1, a portion or all of extract stream 420 may be passed to optional distillation zone 500 comprising distillation column 510 to produce the desorbent stream in conduit 550 comprising the first desorbent component which is recycled to the first adsorptive separation zone 100. Also as illustrated, a portion or all of extract stream 420 may optionally be passed in conduit 460 to extract distillation zone 200 wherein the second and first desorbent components (e.g. toluene and p-DEB, respectively) may be separated and recovered as previously described. Optionally, a portion or all of light stream 230 may be recycled via conduit 270 to provide at least a portion of the second desorbent component stream 20 introduced to second adsorptive separation zone 400. In an embodiment, a first desorbent component from at least one of extract desorbent stream 220, raffinate desorbent stream 320, and second adsorptive separation zone extract stream 420 may be recycled to provide at least a portion of desorbent stream 3 used in the first adsorptive separation zone 100. The C9 aromatic hydrocarbon content and other specifications of the desorbent stream 3 passed into adsorptive separation zone 100 may be controlled by regulating the flow rate of the various streams comprising the first desorbent component among the various flow scheme options. In an embodiment, second adsorptive separation zone 400 may be operated intermittently.

Figure 2:
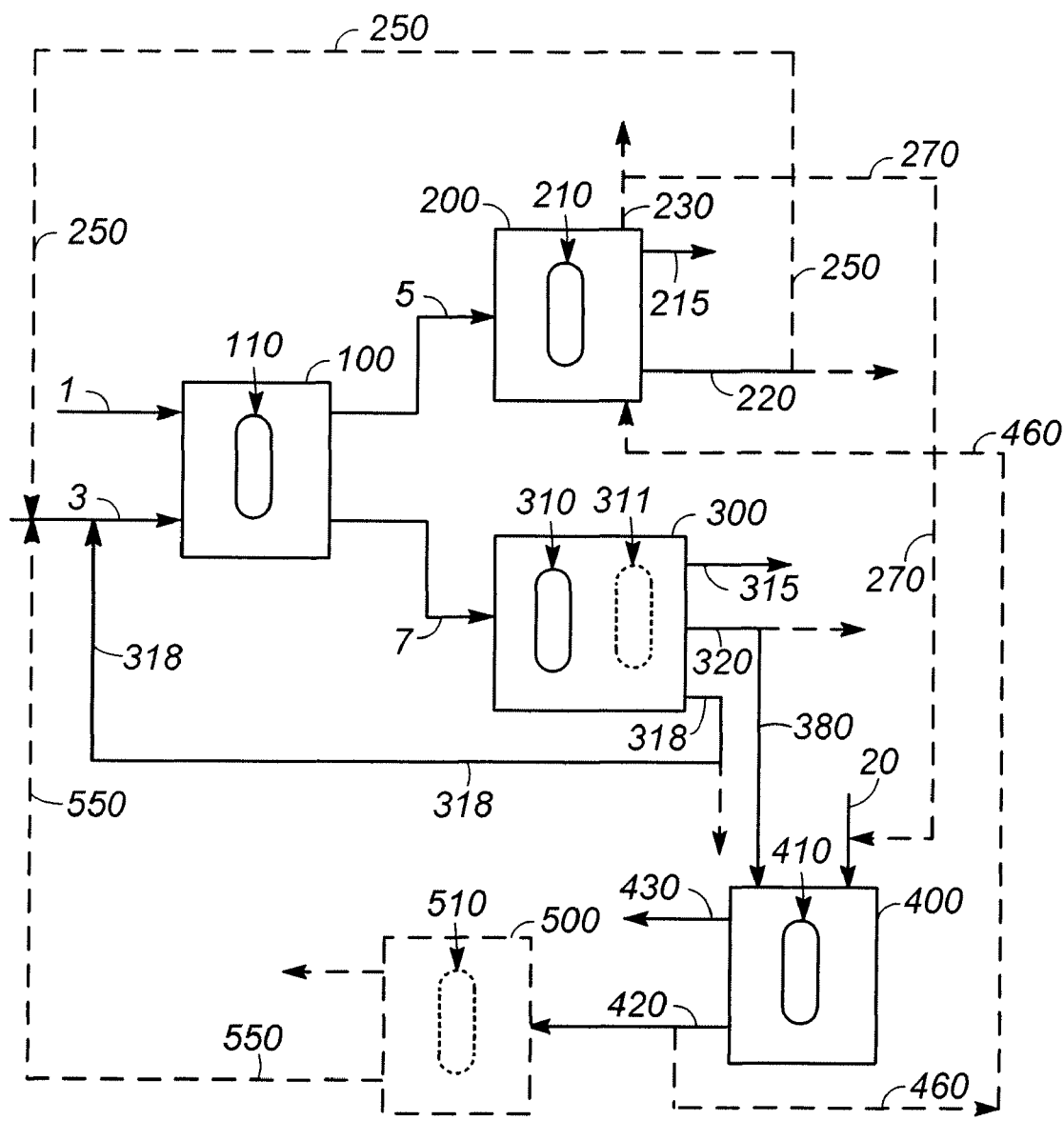
FIG. 2 is a simplified flow scheme illustrating an embodiment of the invention wherein the raffinate distillation zone produces three product streams.

In an embodiment as illustrated in FIG. 2, raffinate distillation zone 300 produces a third effluent stream 318. As previously discussed, three product streams are readily accomplished by those of ordinary skill in the art of distillation. Optional second raffinate distillation column 311 is illustrated in FIG. 2. Raffinate product stream 315 comprises para-xylene depleted C8 aromatic hydrocarbons and desorbent stream 320 comprises the first desorbent component and C9 aromatic hydrocarbons. The third effluent stream 318 has a higher boiling point than desorbent stream 320. Thus, in this embodiment, desorbent stream 320 is intermediate raffinate product stream and stream 318 is a bottoms product from raffinate distillation column 310 and may be referred to as another desorbent stream since it comprises the first desorbent component. Although some portion of the C9 aromatic hydrocarbons in raffinate stream 7 from the first adsorptive separation zone 100 may be in each of streams 315, 318, and 320, the concentration of C9 aromatics (wt %) in desorbent stream 318 is less than the concentration of C9 aromatics (wt %) in desorbent stream 320. In the embodiment illustrated in FIG. 2, at least a portion of the more highly concentrated C9 aromatics is passed through conduits 320 and 380 to be separated from the first desorbent component in second adsorptive separation zone 400. At least a portion of desorbent stream 318 having the lower concentration of C9 aromatic hydrocarbons is recycled to form a portion of desorbent stream 3.

Figure 3:
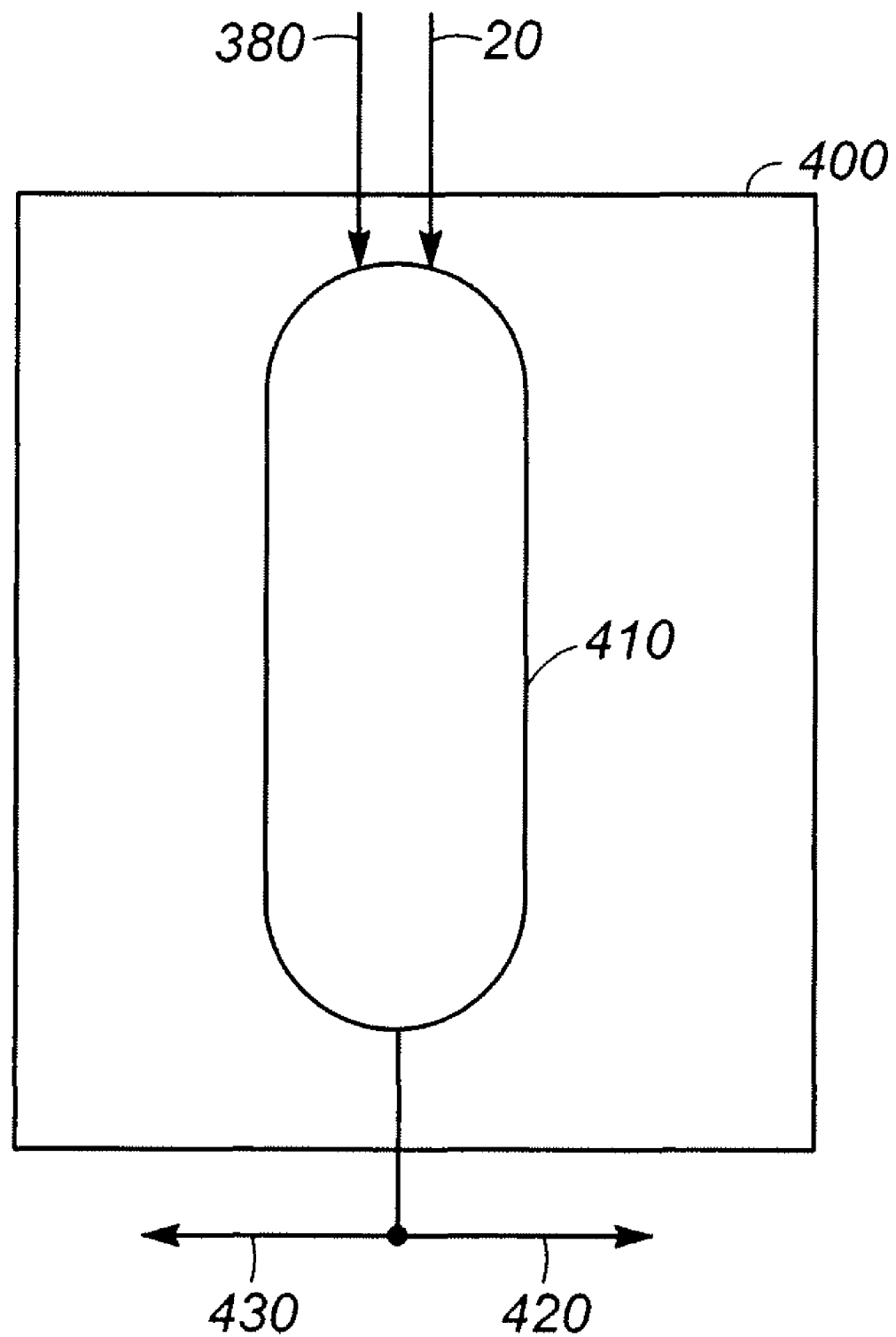
FIG. 3 is a simplified flow scheme of an adsorptive separation zone of the invention illustrating a fixed bed embodiment.

As the invention is not limited by the type or mode of adsorptive separation, those of ordinary skill in the art can readily apply the following descriptions to either adsorptive separation zone though they are described only once. In a batch mode embodiment, an adsorptive separation zone comprises an adsorbent chamber having one or more vessels containing adsorbent in one or more beds. Batch mode operation consists of sequentially introducing feed then desorbent into the adsorbent chamber. The adsorbent is thus subjected to alternate adsorption and desorption steps that produce a raffinate stream and an extract stream which alternately flow out of the adsorbent chamber. In an embodiment, second adsorptive separation zone 400 may operate in a batch mode as illustrated in FIG. 3. Raffinate distillation zone desorbent introduced via conduit 380 is the second adsorptive zone feed and the second adsorptive zone desorbent comprising a second desorbent component is introduced in conduit 20. Thus, conduits 380 and 20 are alternately active in providing fluid communication to adsorptive separation zone 400. Likewise, the raffinate 430 and extract 420 conduits are alternately active in providing fluid communication of the raffinate and extract streams, respectively, from adsorptive separation zone 400. As shown the streams may enter or exit the adsorbent chamber through individual inlets or a common inlet with valves, not shown, controlling the flows as is commonly known.

In swing bed mode, the adsorbent chamber comprises at least two adsorbent beds or vessels each of which is operated in batch mode wherein the adsorbent beds may be operating at different steps of the adsorption/desorption cycle. Swing bed mode may approach continuous production when the adsorbent chamber includes sufficient vessels operating at different points in time of the adsorption/desorption cycle to provide more uniform product quality from the overall adsorptive separation zone. Both the batch mode and swing bed modes are types of fixed bed adsorptive separation processes. In fixed bed adsorptive separations, desorption conditions may be similar to the adsorption conditions. In another embodiment, vapor phase desorption conditions may be used to minimize the amount of desorbent remaining on the adsorbent when feed is introduced to begin the next adsorption/desorption cycle. For example, the desorption pressure may be decreased and/or the temperature may be increased relative to the adsorption conditions. In an embodiment, at least one of first adsorptive separation zone 100 and second adsorptive separation zone 400 is a fixed bed adsorptive separation zone and either or both of zones 100 and 400 may operate in batch or swing bed mode.

Either or both adsorptive separation zones may also operate as a moving bed adsorptive separation system wherein adsorbent moves through the adsorbent chamber while the feed and desorbent streams are introduced to and the extract and raffinate streams are withdrawn from the adsorbent chamber at separate fixed locations.

In an embodiment, at least one of first adsorptive separation zone 100 and second adsorptive separation zone 400 is a simulated moving bed (SMB) adsorptive separation zone. In another embodiment, the first adsorptive separation zone 100 is a simulated moving bed adsorptive separation zone and the second adsorptive separation zone 400 is a fixed bed adsorptive separation zone.

Figure 4:
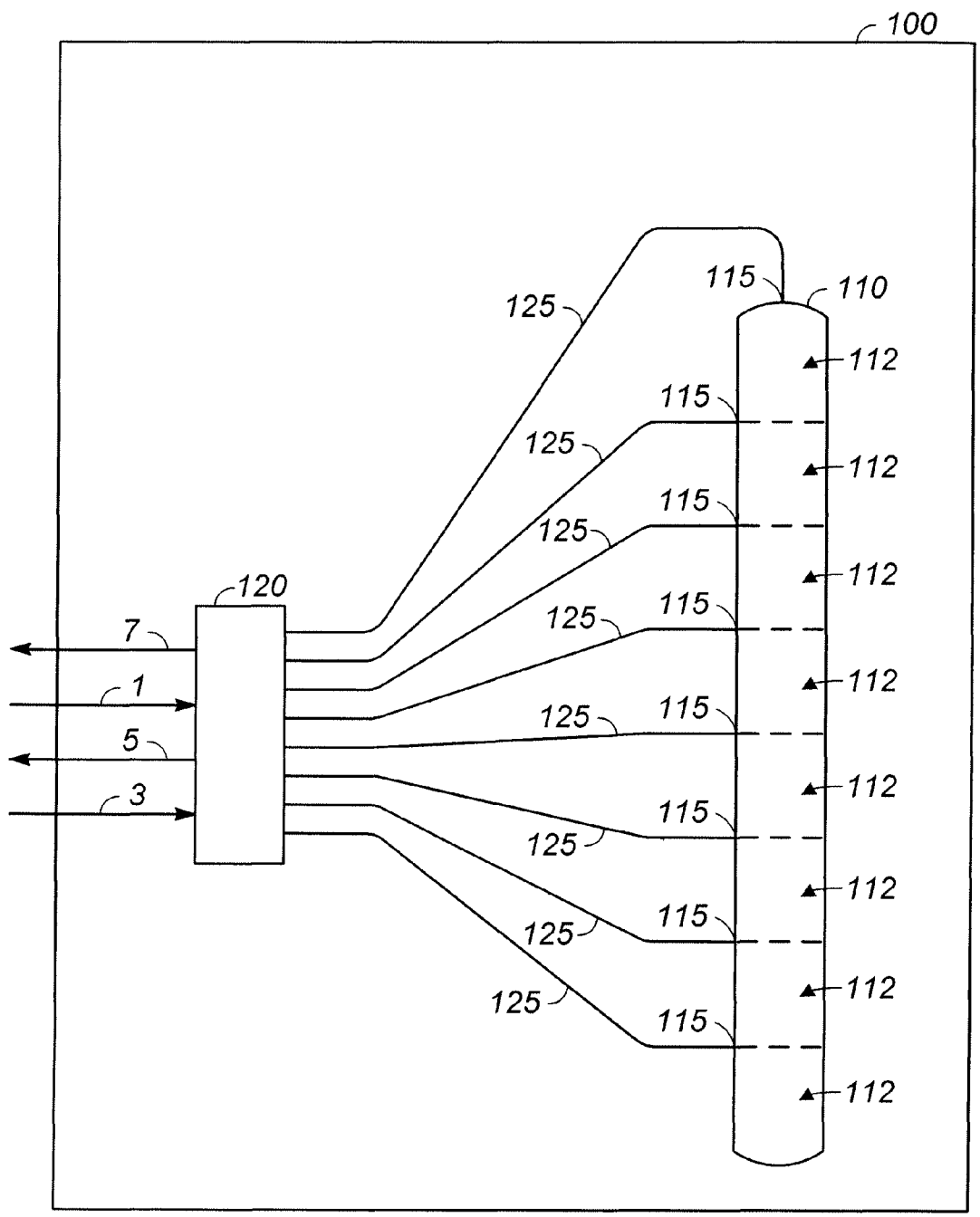
FIG. 4 is a simplified flow scheme of an adsorptive separation zone of the invention illustrating a simulated moving bed embodiment.

FIG. 4, illustrates an embodiment wherein adsorptive separation zone 100 operates as a simulated moving bed (SMB) comprising an adsorbent chamber 110 having at least eight transfer points 115, a fluid distributor 120, and at least one transfer line 125 providing fluid communication between each transfer point and the fluid distributor. The adsorbent chamber 110 contains a number of separate beds 112 of an adsorbent selective for pare-xylene. Each bed is in fluid communication with one of the transfer points. In an embodiment the adsorbent chamber has 16 transfer points. In another embodiment the adsorbent chamber comprises two vessels connected in series, each vessel having 12 transfer points.

In the SMB embodiment, four primary process streams: the feed, desorbent, extract, and raffinate streams are passed simultaneously into and out of the adsorptive separation zone as the adsorption and desorption steps are carried out simultaneously. Feed conduit 1 and desorbent conduit 3 provide fluid communication to fluid distributor 120. The raffinate conduit 7 and extract conduit 5 provide fluid communication from fluid distributor 120. The fluid distributor directs the process streams to and from the adsorbent chamber 110 via transfer lines 125 and transfer points 115. At least four of the transfer line/transfer point pairs are active at a given time. That is, each of the four primary process streams flows through one transfer line/point pair. Additional transfer line/point pairs may also be active when optional streams flow to or from the adsorbent chamber. Examples of optional streams are given in U.S. Pat. No. 3,201,491 and U.S. Pat. No. 4,319,929.

The fluid distributor 120 and an associated controller, not shown, increment the location of the active transfer lines/points periodically along the adsorbent chamber to the next transfer point to simulate movement of the adsorbent in the opposite direction of the transfer point movement. In an embodiment, the locations of the active transfer points are shifted down the adsorbent chamber to simulate upward movement of the adsorbent, and the fluid phase is circulated through the adsorbent chamber in a downward direction. Although not shown in the drawing, the first and last beds in the adsorbent chamber are connected via a conduit and pump to ensure continuous fluid flow in the desired direction. The operating steps, principles, and equipment used in SMB adsorptive separations are well known in the art. U.S. Pat. No. 2,985,589; U.S. Pat. No. 3,310,486; and U.S. Pat. No. 3,686,342 are herein incorporated by reference for their teachings with respect to SMB adsorptive separations.

In SMB adsorptive separation processes, the steps or operational zones in the adsorbent chamber are defined by the position of the input and output streams as follows. Zone 1, the adsorption zone, includes the adsorbent between the feed inlet and raffinate outlet. Zone 2, the purification zone, includes the adsorbent between the feed inlet and the extract outlet and is located upstream of Zone 1. Zone 3, the desorption zone, includes the adsorbent between the extract outlet and the desorbent inlet and is located upstream of Zone 2. Optional Zone 4, a buffer zone, where used includes the adsorbent between the desorbent inlet and the raffinate outlet. Further details on equipment and techniques in an SMB process may be found, for example, in U.S. Pat. No. 3,208,833; U.S. Pat. No. 3,214,247; U.S. Pat. No. 3,392,113; U.S. Pat. No. 3,455,815; U.S. Pat. No. 3,523,762; U.S. Pat. No. 3,617,504; U.S. Pat. No. 4,133,842; and U.S. Pat. No. 4,434,051.

The fluid distributor 120 may be a rotary valve type as described in U.S. Pat. No. 3,040,777; U.S. Pat. No. 3,422,848; and U.S. Pat. No. 4,409,033 or a manifold/multivalve type system as in U.S. Pat. No. 4,434,051. Co-current SMB operations as described in U.S. Pat. No. 4,402,832 and U.S. Pat. No. 4,498,991 may also be used. Equipment utilizing these principles is familiar, in sizes ranging from pilot plant scale as in U.S. Pat. No. 3,706,812 to commercial scale having flow rates from a few cc per hour to many thousands of gallons per hour. The invention may also be practiced in a co-current, pulsed batch process, like that described in U.S. Pat. No. 4,159,284 or in a co-current, pulsed continuous process, like that disclosed in U.S. Pat. Nos. 4,402,832 and 4,478,721.

The invention claimed is:

1. A process for separating para-xylene from a feed stream comprising C8 aromatic hydrocarbons and at least one C9 aromatic hydrocarbon component, the process comprising:
    (a) contacting a first adsorbent comprising a Y zeolite or an X zeolite with the feed stream and a first desorbent stream comprising a first desorbent component having a boiling point of at least about 150° C. in a first adsorptive separation zone to produce a first extract stream comprising para-xylene and the first desorbent component and a first raffinate stream comprising para-xylene depleted C8 aromatic hydrocarbons, the C9 aromatic hydrocarbon component, and the first desorbent component;
    (b) passing the first extract stream to a first extract distillation zone to produce a second desorbent stream comprising the first desorbent component and a para-xylene product stream;
    (c) passing the first raffinate stream to a raffinate distillation zone to produce a third desorbent stream comprising the first desorbent component and the C9 aromatic hydrocarbon component and a raffinate product stream comprising the para-xylene depleted C8 aromatic hydrocarbons; and
    (d) passing at least a portion of the third desorbent stream and a stream comprising a second desorbent component to a second adsorptive separation zone comprising a second adsorbent to produce a second extract stream comprising the first desorbent component and the second desorbent component and a second raffinate stream comprising the C9 aromatic hydrocarbon component and the second desorbent component.

2. The process of claim 1 wherein the first desorbent component is selected from the group consisting of para-diethylbenzene, diethyltoluene, tetralin, tetralin derivatives, indane, naphthalene, methylnaphthalene, and para-dimethylnaphthalene.

3. The process of claim 1 wherein the raffinate distillation zone further produces a fourth desorbent stream, the fourth desorbent stream having a lower wt % concentration of C9 aromatic hydrocarbons than the wt % concentration of C9 aromatic hydrocarbons of the third desorbent stream and recycling at least a portion of the fourth desorbent stream to step (a) as at least a portion of the first desorbent stream.

4. The process of claim 1 further comprising passing the second extract stream to a second extract distillation zone to produce a fifth desorbent stream comprising the first desorbent component and recycling at least a portion of the fifth desorbent stream to step (a) as at least a portion of the first desorbent stream.

5. The process of claim 1 further comprising recycling at least a portion of the second desorbent stream to step (a) as at least a portion of the first desorbent stream.

6. The process of claim 1 further comprising recycling a portion of the third desorbent stream to step (a) as at least a portion of the first desorbent stream.

7. The process of claim 1 further comprising recycling at least a portion of the second extract stream to the first extract distillation zone.

8. The process of claim 1 wherein the second adsorbent comprises an MFI type zeolite.

9. The process of claim 1 wherein the second adsorbent comprises a Y zeolite or an X zeolite.

10. The process of claim 9 wherein the first desorbent component is para-diethylbenzene.

11. The process of claim 1 wherein the feed stream comprises no more than about 25 wt % C9 aromatic hydrocarbons.

12. The process of claim 1 wherein the first desorbent stream comprises no more than about 25 wt % C9 aromatic hydrocarbons.

13. The process of claim 1 wherein the feed stream further comprises para-methylethylbenzene in an amount not more than about 0.05 wt % of the para-xylene in the feed stream.

14. The process of claim 1 wherein the feed stream further comprises no more than about 10 ppm-mass of C10+ aromatic hydrocarbons.

15. The process of claim 1 wherein the first adsorbent zeolite further comprises barium.

16. The process of claim 1 wherein the first adsorptive separation zone is a simulated moving bed adsorptive separation zone.

17. The process of claim 16 wherein the simulated moving bed adsorptive separation zone operates in counter-current mode at a temperature ranging from about 20° C. to about 300° C. and a pressure ranging from about 1 barg to about 40 barg.

18. A process for separating para-xylene from a feed stream comprising C8 aromatic hydrocarbons and C9 aromatic hydrocarbons including para-methylethylbenzene, the process comprising:
    (a) contacting a first adsorbent comprising a Y zeolite or an X zeolite with the feed stream and a first desorbent stream comprising para-diethylbenzene in a simulated moving bed adsorptive separation zone to produce a first extract stream comprising para-xylene, para-methylethylbenzene, and para-diethylbenzene and a first raffinate stream comprising para-xylene depleted C8 aromatic hydrocarbons, para-methylethylbenzene depleted C9 aromatic hydrocarbons, and para-diethylbenzene;

(b) passing the first extract stream to a first extract distillation zone to produce a second desorbent stream comprising para-diethylbenzene and a para-xylene product stream;

(c) passing the first raffinate stream to a raffinate distillation zone to produce a third desorbent stream comprising para-diethylbenzene and the para-methylethylbenzene depleted C9 aromatic hydrocarbons and a raffinate product stream comprising the para-xylene depleted C8 aromatic hydrocarbons; and (d) passing at least a portion of the third desorbent stream and a stream comprising a second desorbent component to a fixed bed adsorptive separation zone comprising a second adsorbent to produce a second extract stream comprising para-diethylbenzene and the second desorbent component and a second raffinate stream comprising C9 aromatic hydrocarbons and the second desorbent component.

19. The process of claim 18 wherein the second adsorbent comprises a zeolite selected from the group consisting of a Y zeolite, an X zeolite and an MFI type zeolite; and the second desorbent component is selected from the group consisting of benzene, toluene, tetralin, naphthalene, methylnaphthalene, and para-dimethylnaphthalene.

20. The process of claim 19 further comprising recycling at least a portion of the second extract stream to the first extract distillation zone.

* * * * *